(12) United States Patent
Finch et al.

(10) Patent No.: US 7,247,175 B2
(45) Date of Patent: Jul. 24, 2007

(54) METHOD OF PURIFYING A PESTICIDE

(75) Inventors: Charles W. Finch, Garner, NC (US); Kenneth E. Fersch, Apex, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 531 days.

(21) Appl. No.: 10/397,765

(22) Filed: Mar. 26, 2003

(65) Prior Publication Data
US 2003/0199394 A1    Oct. 23, 2003

(51) Int. Cl.
*B01D 9/00*    (2006.01)
(52) U.S. Cl. ....................... 23/300; 23/295 R
(58) Field of Classification Search ........... 23/300, 23/295 R; 210/664; 424/409, 417, 421
See application file for complete search history.

(56) References Cited

U.S. PATENT DOCUMENTS

| | | | | |
|---|---|---|---|---|
| 3,956,500 A | * | 5/1976 | Durden et al. ............. | 514/433 |
| 4,935,527 A | * | 6/1990 | Kitagawa et al. ........... | 548/966 |
| 5,654,258 A | | 8/1997 | Park et al. .................. | 504/347 |
| 5,869,517 A | | 2/1999 | Müller et al. ............... | 514/407 |
| 6,225,372 B1 | * | 5/2001 | Lykke et al. ................ | 523/201 |

* cited by examiner

*Primary Examiner*—Edward M. Johnson
(74) *Attorney, Agent, or Firm*—Novak Druce & Quigg, LLP

(57) ABSTRACT

The present invention describes a method of purifying a pesticide that includes: a) melting a pesticide, wherein the pesticide includes at least one active ingredient and at least one impurity capable of inhibiting crystallization; b) coating the pesticide on a substrate to form a pesticide particle; c) substantially reducing the amount of crystallization inhibiting impurity by an azeotropic method; and d) crystallizing the pesticide. In another embodiment, the present invention includes a method of purifying a pesticide as described above, such that the pesticide has a melting point of not more than about 90° C. Also included in the invention is the product produced by the above process for the pesticide, methyl N-(2-{[1-(4-chlorophenyl)-1H-pyrazol-3-yl]oxymethyl}phenyl)N-methoxy carbamate.

20 Claims, 2 Drawing Sheets

2A

2B

2C

2D

2E

2F

2G

2H

2I

METHOD OF PURIFYING A PESTICIDE

FIELD OF THE INVENTION

The present invention relates to methods of purifying pesticides, in particular, the present invention relates to purifying pesticides that include at least one impurity capable of inhibiting crystallization.

BACKGROUND OF THE INVENTION

Pesticides are used in various formulations, including dry formulations, such as wettable powders, granules and tablets. These dry formulations have several advantages; one of which is the ease of use. For good biological efficacy, it is generally desirable that the solid pesticides reduce in size upon mixing with water. However, for active pesticide ingredients with low melting points, this particle size reduction is difficult to achieve due to the lack of defined crystalline structure, thereby frustrating milling the pesticide to achieve particle size reduction. Further, the same problems are shared by mixed preparations containing a pesticide having a low melting point active ingredient and a pesticide having a high melting point active ingredient. As such, there is a need for purified pesticides in order to enhance particle size reduction.

SUMMARY OF THE INVENTION

As embodied and broadly described herein, this invention, in one aspect, relates to a method of purifying a pesticide that includes: a) melting a pesticide, wherein the pesticide includes at least one active ingredient and at least one impurity capable of inhibiting crystallization; b) coating the pesticide on a substrate to form a pesticide particle; c) substantially reducing the amount of crystallization inhibiting impurity by an azeotropic method; and d) crystallizing the pesticide.

In another aspect, the present invention includes a method of purifying a pesticide as described above, such that the pesticide has a melting point of not more than about 90° C.

Advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

DETAILED DESCRIPTION

Figure 1:
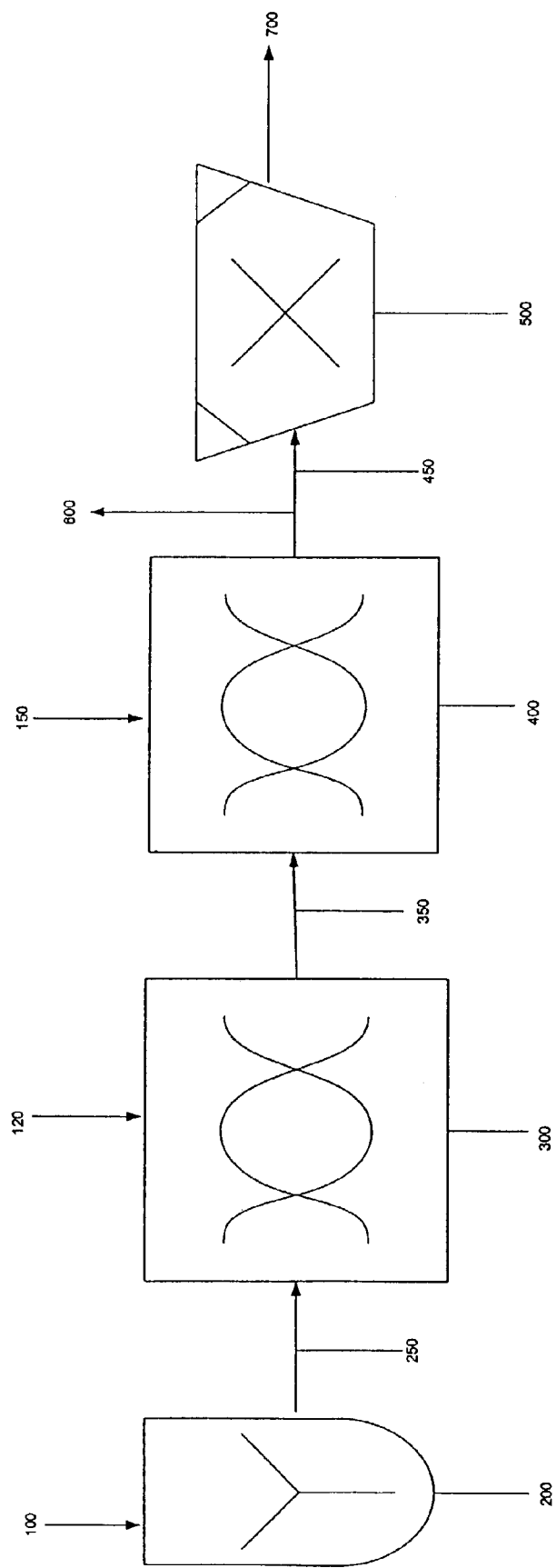
FIG. 1 is a process diagram of a preferred embodiment of the invention.
Figure 2A:
FIGS. 2A–2I are photographs depicting the results from Example 1.
Figure 2B:
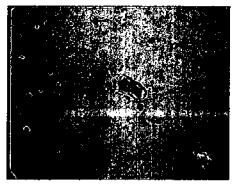
Figure 2C:
Figure 2D:
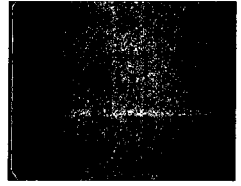
Figure 2E:
Figure 2F:
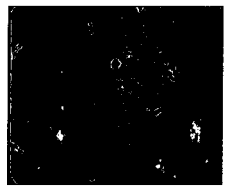
Figure 2G:
Figure 2H:
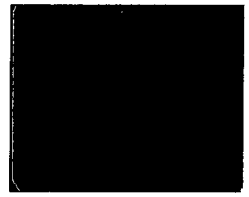
Figure 2I:

The present invention may be understood more readily by reference to the following detailed description of exemplary embodiments of the invention and the examples included therein.

Before the present compounds, compositions, and methods are disclosed and described, it is to be understood that the pesticide manufacture is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

The term "pesticide" refers to a mixture of one or more active ingredients and one or more impurities.

By "technical grade active ingredient pesticide" is meant that the mixture of active ingredients and impurities includes less than 10 wt. % impurities, preferably less than 5 wt. % impurities. The impuries may be any impure ingredient, including but not limited to, reaction by-products, intermediates, starting materials, and solvents.

"Salt" as used herein includes salts that can form with, for example, amines, metals, alkaline earth metal bases or quaternary ammonium bases, including zwitterions. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, metrab, acetate, carbonate, hydride, and hydroxide.

The present invention includes a method of purifying a pesticide that includes: a) melting a pesticide, wherein the pesticide includes at least one active ingredient and at least one impurity capable of inhibiting crystallization; b) coating the pesticide on a substrate to form a pesticide particle; c) substantially reducing the amount of crystallization inhibiting impurity by an azeotropic method; and d) crystallizing the pesticide.

Any pesticide may be employed. In one embodiment, the pesticide is a technical grade active ingredient pesticide "TGAI pesticide." The TGAI pesticide may have a low melting point, including but not limited to, TGAI pesticides with melting points of not more than 120° C., preferably not more than 90° C., and more preferably not more than 80° C.

The active ingredient of the pesticide can be used for controlling harmful insects, acarines, nematodes, fungi, and undesirable plants. In one embodiment, the active ingredient is a 2-[(dihydro)pyrazolyl]-3'-oxymethylene]-anilide of formula (I):

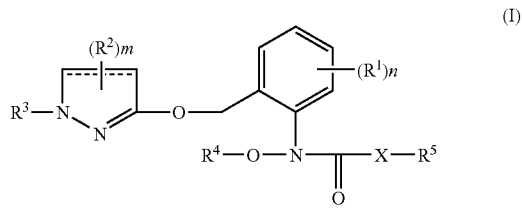

wherein —is a single or double bond and the indices and the substituents have the following meanings:

n is 0, 1, 2, 3 or 4, it being possible for the substituents $R^1$ to be different if n is greater than 1;

m is 0, 1 or 2, it being possible for the substituents $R^2$ to be different if m is greater than 1;

X is a direct bond, O or $NR^a$;

$R^a$ is hydrogen, alkyl, alkenyl, alkynyl, cycloalkyl or cycloalkenyl;

$R^1$ is nitro, cyano, halogen, unsubstituted or substituted alkyl, alkenyl, alkynyl, alkoxy, alkenyloxy, alkynyloxy or in the case where n is 2, additionally is an unsubstituted or substituted bridge bonded to two adjacent ring atoms and containing three to four members from the group consisting of 3 or 4 carbon atoms, 1 to 3 carbon atoms and 1 or 2 nitrogen, oxygen and/or sulfur atoms, this bridge together with the ring to which it is bonded being able to form a partly unsaturated or aromatic radical;

$R^2$ is nitro, cyano, halogen, alkyl, haloalkyl, alkoxy, alkylthio or alkoxycarbonyl;

$R^3$ is unsubstituted or substituted alkyl, alkenyl or alkynyl; an unsubstituted or substituted, saturated or mono- or diunsaturated ring which, in addition to carbon atoms, can contain one to three of the following heteroatoms as ring members: oxygen, sulfur and nitrogen, or an unsubstituted or substituted, mono- or binuclear aromatic radical which, in addition to carbon atoms, can contain one to four nitrogen atoms or one or two nitrogen atoms and one oxygen or sulfur atom or one oxygen or sulfur atom as ring members;

$R^4$ is hydrogen, unsubstituted or substituted alkyl, alkenyl, alkynyl, cycloalkyl, cycloalkenyl, alkylcarbonyl or alkoxycarbonyl; and $R^5$ is alkyl, alkenyl, alkynyl, cycloalkyl or cycloalkenyl, or in the case where X is $NR^a$, additionally is hydrogen; and salts and esters thereof.

Desirably, in the formula (I), n is 0 or 1; m is 0 or 1; X is O; $R^1$ is unsubstituted or substituted $C_1$–$C_4$ alkyl, $C_2$–$C_4$ alkenyl, or $C_1$–$C_4$ alkoxy; $R^2$ is $C_1$–$C_4$ alkyl, $C_1$–$C_4$ haloalkyl, or $C_1$–$C_4$ alkoxy; $R^3$ is an unsubstituted or substituted benzene; $R^4$ is hydrogen, unsubstituted or substituted $C_1$–$C_4$ alkyl, $C_2$–$C_4$ alkenyl, or $C_1$–$C_4$ alkylcarbonyl; and $R^5$ is $C_1$–$C_4$ alkyl or $C_2$–$C_4$ alkenyl.

More desirably, the active ingredient is methyl N-(2-{[1-(4-chlorophenyl)-1H-pyrazol-3-yl]oxymethyl}phenyl)N-methoxy carbamate, pyraclostrobin, as represented by formula (II):

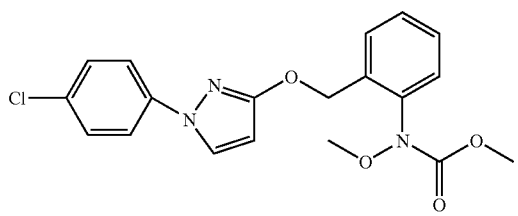

(II)

The impurity or impurities present in the pesticide or TGAI pesticide may be any impurity including reaction by-products, intermediates, starting materials, and solvents. In one embodiment, the active ingredient chemically decomposes at temperatures within 50° C. of the normal boiling point of the crystallizing-inhibiting impurity. Such an impurity makes the pesticide purification difficult. At least one of the impurities should be capable of being removed azeotropically, such as by vacuum distillation, heat, or low pressure evaporation.

The azeotropes may include binary or ternary mixtures comprising water, alcohols, hydrocarbons, substituted hydrocarbons, ethers, esters, organic acids, inorganic acids, ketones, aldehydes, amines, and mixtures thereof. These azeotropes may be formed solely from impurities present in the pesticide or the pesticide may be mixed with an azeotrope-forming compound, such as a solvent as listed above. This mixture may be made either before or after the pesticide is melted.

For example, pyraclostrobin has a melting point of about 64° C. In one embodiment, the TGAI pyraclostrobin includes toluene and water, effectively lowering the melting point to about 40° C. Toluene, which has a boiling point of about 110° C., is capable of forming an azeotrope with water, which has a boiling point of about 84° C. As such, the toluene and water impurities may be removed by azeotropic separation methods.

Azeotropic separation is assisted by coating melted pesticide onto a substrate. Desirably, the coating is a thin film that provides increased surface area for azeotrope transport. As such, any substrate may be used that is compatible with the pesticide. The substrate may be any natural or synthetic organic or inorganic ingredient that facilitates dispersion of the composition or compound. Exemplary substrates include lignin sulfonate, synthetic silicates, silica, urea, lactose, ammonium sulfate, sucrose, sodium chloride, sodium sulfate, clay, diatomite, terra alba, talc, calcium carbonate, attapulgite and water-soluble polymers such as hydroxypropyl cellulose, methyl cellulose, methylethyl cellulose, and polyvinyl alcohol.

The coating process of the melted pesticide onto a substrate can be carried out in different ways:
  i) Without any solvent
  ii) In the presence of an organic solvent. The substrate is dispersed in an organic solvent before the melted active ingredient is added. As organic solvents aromatic or aliphatic hydrocarbons or chlorinated hydrocarbons, alcohols or mixtures of these solvents can be used.
  iii) In the presence of water. The substrate is dispersed in water and the melted active ingredient is added as disclosed in DE 200 1792.

The azeotropic separation is accomplished by heating the pesticide-coated substrate to the appropriate temperature. This may be accomplished by preheating the substrate and adding the melted pesticide to the preheated substrate.

Substantially removing the impurities allows for a quickened crystallization rate. This crystallization may take place by chilling the pesticide to a temperature below that used for the azeotropic separation. In one embodiment, the crystallized pesticide comprises not more than 5 wt. % total impurities; preferably the crystallization inhibiting impurity is reduced to not more than 0.1 wt. %, more preferably to not more than 0.05 wt. %. Adequate crystallization may take from 1 hour to 72 hours, preferably from 1 hours to 24 hours.

After the pesticide is crystallized, the pesticide particle may be reduced in size. Any size reduction method that is suitable may be employed. Exemplary methods include impact methods and fluid energy methods, such as air mill, air jet mill, pin mill, hammer mill, and the like.

The pesticide particles may be reduced to any size feasible. Typically, small particle size is a factor in biological efficacy. Therefore, in preferred embodiments, the pesticide particle size is not more than 50 μm, more preferably not more than 30 μm, and even more preferably not more than 10 μm.

Other optional components may be admixed with pesticides either before or after azeotropic separation to facilitate the application and/or effectiveness of the active ingredient. To this end, optional components that may be added include surfactants, including cationic and anionic surfactants; dispersing agents; wetting agents; antifoaming agents; antimicrobial agents; antioxidants; buffers; dyes; perfumes; stabilizing agents; and water soluble salts.

Pesticides of this invention may also be mixed with other active ingredients, for example fertilizers such as ammonium nitrate, urea, potash, and superphosphate; phytotoxicants and plant growth regulators; safeners; and pesticides. These additional ingredients may be mixed with pesticides either before or after azeotropic separation.

Compositions of the present invention may be present in any effective dry formulation, including, but not limited to, powders; brickettes; granules; tablets; and the like.

Powders, including dusting powders or granules and water dispersible powders, granules or grains contain at least one active ingredient and an inert solid extender or carrier, such as kaolin, bentonite, dolomite, calcium carbonate, talc, powdered magnesia, Fuller's earth, gypsum, diatomaceous earth and China clay. Water dispersible powders, granules and grains typically also include one or more wetting and dispersing agents, such as surfactants.

The composition of this invention may comprise 0.5 wt. % to 40 wt. %, preferably 2 wt. % to 30 wt. % by weight of the pesticide; 1 wt. % to 50 wt. %, preferably 2 wt. % to 40 wt. % of solid carrier and/or substrate; and 10 wt. % to 30 wt. %. other ingredients.

The compounds useful in the present invention may be readily synthesized using techniques generally known to synthetic organic chemists. The compositions may be prepared in known manner, for example by homogeneously mixing or grinding the active ingredients with other ingredients. Additional components may be admixed with the composition at any point during the process, including during and/or after any mixing step of the herbicide components.

Referring now to FIG. 1, which is one preferred embodiment of the present invention, the present invention provides a method of purifying a pesticide. The process embodied in FIG. 1 demonstrates the purification of a TGAI pesticide, methyl N-(2-{[1-(4-chlorophenyl)-1H-pyrazol-3-yl]oxymethyl}phenyl)N-methoxy carbamate 100, which is melted in melt tank 200. The melt tank 200 is heated to at least 70° C., preferably to between about 85° C. and about 90° C. This heating may occur by any suitable method, including jacketing the mixer 200 and using hot water as the jacket heat transfer liquid. Preferably, the melt tank 200 includes a mixing device to more evenly distribute the heat.

Separately, in a blender 300, ten parts of precipitated silica are charged, along with four parts of a liginin sulfonate 120. Preferably, the blender 300 is a batch ribbon, paddle, plow, or the like, to allow for mixing. In one embodiment, the blender is equipped with a high shear impact chopper assembly, such as an intensifying bar. This assembly allows the batch to achieve as high a batch temperature as possible in as short a time as possible.

The blender 300 may be pre-heated to a temperature close to the melt tank 200 temperature.

The molten pesticide in the melt tank 200 is added to the blender 300 by manual means, such as pouring, or by pipe, hose, spray nozzle and/or pump connection 250. Preferably, the pesticide is added at an even rate. Moreover, the piping, hosing, spray nozzle, and/or pump 250 is preferably heated to maintain flowablility.

In one embodiment, the blender 300 is jacketed. The time to reach temperature is a function of temperature of the jacket, mixing rate, volume of materials, and starting temperature of materials. As such, these parameters are adjustable to meet the needs of the batch processing. In one embodiment, the mixing rate, as measured by tip speed, is at least 10 m/s, preferably at least 30 m/s.

The blender 300 may have airflow or vacuum applied to remove volatile impurities. Any suitable pressure may be used.

The blending time is also adjustable based on the uniformity of the mix, the temperature of the mix, and the type of blender. In the embodiment of FIG. 1, it is desirable to exceed a batch temperature of 84° C., the azeotropic separation temperature for toluene-water. Typically, about 30 minutes of mixing time is employed.

The pesticide 100 coats the substrate 120 in the blender 300 to form a pesticide particle. The pesticide particles are then transported 350 to a second blender 400. Other ingredients 150 may also be added to the blender 400. Preferably, the blender 400 is chilled to cool and initiate crystal growth, such as to not more than 30° C., preferably to not more than 25° C. As such, the blender 400 may be jacketed and contain a mixing element, as with the blender 300. The time to crystallize is dependent upon several factors including temperature and amount of solvent impurity.

The pesticide particles are then collected 600 or transported 450 to an impact device 500. Any suitable impact device 500 may be used, including air mills, jet mills, and the like. The pesticide particles may be subjected to multiple passes through the impact device 500, which reduces the particle size and may also reduce the amount of impurity in the pesticide. Typically, particle sizes are reduced to not more than 10 μm.

After particle size reduction in the impact device 500, the particles are collected 700 for use in making the appropriate pesticide formulations.

Experimental:

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, percent is percent by weight given the component and the total weight of the composition, temperature is in ° C. or is at ambient temperature, and pressure is at or near atmospheric.

EXAMPLE 1

Impurity Effects on Crystallization

Batch 1A and 1B were melted at about 80° C. and allowed to crystallize for 1 week at temperatures of 25° C. and 50° C., at which time a sample of the pesticide was placed on a microscope slide and covered with a glass plate. The slide was placed in storage and observed at 24 hours and 168 hours. The visual observations are noted in Table 1 after observation with a microscope under 400× magnification using polarized light and a wave plate. Photographs of these samples were taken as depicted in FIG. 2.

Batch 1A: methyl N-(2-{[1-(4-chlorophenyl)-1H-pyrazol-3-yl]oxymethyl}phenyl)N-methoxy carbamate 92.99%; toluene 0.094%

Batch 1B: methyl N-(2-{[1-(4-chlorophenyl)-1H-pyrazol-3-yl]oxymethyl}phenyl)N-methoxy carbamate 96.90%; toluene 0.510%

TABLE 1

Visual Observations of Crystal Formation

| Batch | Storage Temperature (° C.) | Observation Time (hr) | Observation | Figure 2 Photograph |
|---|---|---|---|---|
| 1A, 1B | N/A | 0 | crystals not present | 2A |
| 1A | 25 | 24 | crystals not present | 2B |
| 1A | 25 | 168 | crystals present | 2F |
| 1A | 50 | 24 | crystals present | 2C |
| 1A | 50 | 168 | crystals present | 2G |
| 1B | 25 | 24 | crystals not present | 2D |
| 1B | 25 | 168 | crystals not present | 2H |
| 1B | 50 | 24 | crystals not present | 2E |
| 1B | 50 | 168 | crystals not present | 2I |

Batch 1A and 1B were observed for crystal formation at various storage temperatures. The crystal growth percent was measured by determining the melt energy for the sample and multiplying by 100% and dividing by 61.13 j/g (the amount of heat that must be added to melt the fully crystallized product). The results are shown in Table 2.

TABLE 2

Crystal Growth Rate

| | Crystal Growth Rate (%) | | | | | |
|---|---|---|---|---|---|---|
| | Batch 1A | | | Batch 1B | | |
| Days | 40° C. | 25° C. | 5° C. | 40° C. | 25° C. | 5° C. |
| 0.00 | 0.00 | 0.00 | 0.00 | 0.00 | 0.00 | 0.00 |
| 0.13 | na | na | 1.58 | 0.00 | 0.00 | 0.00 |
| 1.00 | 0.67 | 1.09 | 2.65 | 0.00 | 0.00 | 0.00 |
| 2.00 | 0.01 | 1.75 | 3.30 | 0.00 | 0.00 | 0.78 |
| 3.00 | 0.01 | 5.65 | 9.31 | 1.16 | 0.00 | 1.63 |

EXAMPLE 2

Effect of Milling on Impurities

Batch 2A, 2B and 2C, which were produced from Batch 1B, were subjected to the process of the present invention. A jet mill was used after the product was crystallized as indicated in Table 3.

TABLE 3

Effect of Milling on Impurities

| Batch | Toluene (%) | Process Conditions | Particle Size (μm) |
|---|---|---|---|
| 2A | 0.013 | Azeotrope heated above 84° C. but below 90° C.; Not milled after crystallization | 31.8 |
| 2B | 0.002 | Azeotrope heated above 84° C. but below 90° C.; Milled after crystallization with 1 pass at 75 lb/hr | 11.9 |

TABLE 3-continued

Effect of Milling on Impurities

| Batch | Toluene (%) | Process Conditions | Particle Size (μm) |
|---|---|---|---|
| 2C | 0.002 | Azeotrope heated above 84° C. but below 90° C; Milled after crystallization with 2 passes at 50 lb/hr | 7.7 |

EXAMPLE 3

Effect of Impurities on Crystallization

Batch 3A and 3B were produced from Batch 1B, and Batch 3C was produced from Batch 1A. [PLEASE VERIFY.] All three batches were subjected to the process of the present invention. The time to crystallize was measured as indicated in Table 4.

TABLE 4

Effect of Impurities on Crystallization

| Batch | Toluene Content | Time Exceeding 84° C. | Time to Crystallize (optical) |
|---|---|---|---|
| 3A | 0.013% | 25 minutes | <3 hours |
| 3B | 0.016% | 28 minutes | <3 hours |
| 3C | 0.020% | 0 minutes | ~2 weeks |

EXAMPLE 4

Effect of Impurities on Physical State and Milling

Batch 4A and 4B, produced from Batch 1B, were subjected to the process of the present invention. [PLEASE VERIFY.] The time to crystallize and particle size were measured as indicated in Table 5.

TABLE 5

Effect of Impurities on Physical State and Milling

| Batch | Toluene Content Observed | Sample History | Time Exceeding 84° C. | Time to Crystallize (optical) | Particle Size (um) |
|---|---|---|---|---|---|
| 4A | 0.002% | Airmilled after crystalline | 28 minutes | <3 hours | 8.0 |
| 4B | 0.020% | Airmilled while not crystalline | 0 minutes | ~2 weeks | 21.4 |

EXAMPLE 5

Effect of Impurities on Physical State and Milling Process

Batch 5A and 5B were produced from Batch 1B, and Batch 5C was produced from Batch 1A. [PLEASE VERIFY.] All three batches were subjected to the process of the present invention, with varying milling processes. The time to crystallize and particle size were measured as indicated in Table 6.

TABLE 6

Effect of Impurities on Physical State and Milling Process

| Batch | Toluene Content Observed | Sample History | Time Exceeding 84° C. | Time to Crystallize (optical) | Partical Size (um) |
|---|---|---|---|---|---|
| 5A | 0.016% | Not airmilled, as above | 28 minutes | <3 hours | 20.6 |
| 5B | 0.002% | 5A airmilled after crystalline | as above | as above | 8.0 |
| 5C | 0.020% | Airmilled while not crystalline | 0 minutes | ~2 weeks | 21.4 |

EXAMPLE 6

Effect of Impurities on Milling

Batch 6A, 6B, and 6C were produced from Batch 1B. [PLEASE VERIFY.] The batches were subjected to the process of the present invention. The particle sizes were measured as indicated in Table 7.

TABLE 7

Effect of Impurities on Milling

| Process Conditions | Batch | 6A | 6B | 6C |
|---|---|---|---|---|
| | Time Batch Temperature Exceeded 84° C. | 0 minutes | 28 minutes | 25 minutes |
| | Toluene Content Product (%) | 0.020% | 0.016% | 0.013% |
| | Batch aging time prior to airmilling | ~14 days | same day | 6 days |
| | Physical state at time of airmilling | not crystalline | mostly crystalline | completely crystalline |
| First pass airmilling | Volume Weight Mean VMD (PSS) | na | 8.0 μm | 7.7 μm |
| | D$_{50}$ (Malvern) | na | 8.9 μm | 8.1 μm |
| Second Pass airmilling | Volume Weight Mean VMD (PSS) | 18.8 μm | 7.1 μm | 5.9 μm |
| | D$_{50}$ (Malvern) | 13.9 μm | 7.7 μm | 4.3 μm |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of purifying a pesticide comprising:
   a) melting a pesticide, wherein the pesticide comprises at least one active ingredient and at least one impurity capable of inhibiting crystallization;
   b) coating the melted pesticide on a substrate to form a pesticide particle;
   c) substantially reducing the amount of crystallization inhibiting impurity by an azeotropic method; and
   d) crystallizing the pesticide.

2. The method of claim 1, wherein the active ingredient is a compound of formula (I):

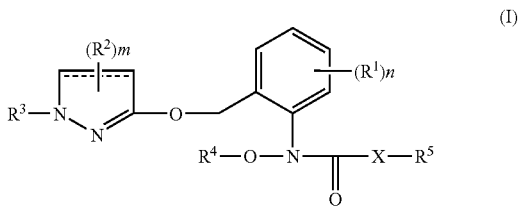

wherein - - - - is a single or double bond and the indices and the substituents have the following meanings:

n is 0, 1, 2, 3 or 4, it being possible for the substituents $R^1$ to be different if n is greater than 1;

m is 0, 1 or 2, it being possible for the substituents $R^2$ to be different if m is greater than 1;

X is a direct bond, 0 or $NR^a$;

$R^a$ is hydrogen, alkyl, alkenyl, alkynyl, cycloalkyl or cycloalkenyl;

$R^1$ is nitro, cyano, halogen, unsubstituted or substituted alkyl, alkenyl, alkynyl, alkoxy, alkenyloxy, alkynyloxy or in the case where n is 2, additionally is an unsubstituted or substituted bridge bonded to two adjacent ring atoms and containing three to four members from the group consisting of 3 or four carbon atoms, 1 to 3 carbon atoms and 1 or 2 nitrogen, oxygen and/or sulfur atoms, this bridge together with the ring to which it is bonded being able to form a partly unsaturated or aromatic radical;

$R^2$ is nitro, cyano, halogen, alkyl, haloalkyl, alkoxy, alkylthio or alkoxycarbonyl;

$R^3$ unsubstituted or substituted alkyl, alkenyl or alkynyl; an unsubstituted or substituted, saturated or mono or diunsaturated ring which, in addition to carbon atoms, can contain one to three of the following heteroatoms as ring members: oxygen, sulfur and nitrogen, or an unsubstituted or substituted mono- or binuclear aromatic radical which, in addition to carbon atoms, can contain one to four nitrogen atoms or one or two nitrogen atoms and one oxygen or sulfur atom or one oxygen or sulfur atom as ring members;

$R^4$ is hydrogen, unsubstituted or substituted alkyl, alkenyl, alkynyl, cycloalkyl, cycloalkenyl, alkylcarbonyl or alkoxycarbonyl; and $R^5$ is alkyl, alkenyl, alkynyl, cycloalkyl or cycloalkenyl, or in the case where X is $NR^a$, additionally is hydrogen;

or the salt or ester thereof.

3. The method of claim 2, wherein formula (I):

n is 0 or 1;
m is 0 or 1;
X is 0;
$R^1$ is unsubstituted or substituted $C_1$–$C_4$ alkyl, $C_2$–$C_4$ alkenyl, or $C_1$–$C_4$ alkoxy;
$R^2$ is $C_1$–$C_4$ alkyl, $C_1$–$C_4$ haloalkyl, or $C_1$–$C_4$ alkoxy;
$R^3$ is an unsubstituted or substituted benzene;
$R^4$ is hydrogen, unsubstituted or substituted $C_1$–$C_4$ alkyl, $C_2$–$C_4$ alkenyl, or $C_1$–$C_4$ alkylcarbonyl; and
$R^5$ is $C_1$–$C_4$ alkyl or $C_2$–$C_4$ alkenyl.

4. The method of claim 1, wherein the active ingredient is methyl N-(2-{[1-(4chlorophenyl)-1H-pyrazol-3-yl] oxymethyl}phenyl)N-methoxy carbamate.

5. The method of claim 1, wherein the method further comprises mixing the pesticide with a solvent before coating the pesticide on the substrate.

6. The method of claim 5, wherein the solvent is water.

7. The method of claim 1, wherein the active ingredient chemically decomposes at temperatures within 50° C. of the normal boiling point of the impurity.

8. The method of claim 1, wherein the azeotropic method is accomplished by vacuum distillation, heat, or low pressure evaporation.

9. The method of claim 1, wherein the substrate is lignin sulfonate, synthetic silicates, silica, urea, lactose, ammonium sulfate, sucrose, sodium chloride, sodium sulfate, clay, diato mite, terra alba, talc, calcium carbonate, attapulgite, water soluble polymer, or combinations thereof.

10. The method of claim 9, wherein the substrate is lignin sulfonate, silica, or a combination thereof.

11. The method of claim 1, further comprising reducing the size of the crystallized pesticide particle by an impact method.

12. The method of claim 1, wherein the crystallized pesticide has a particle size of not more than 10 μm.

13. The method of claim 1, wherein the crystallized pesticide comprises less than 0.1 wt. % of an impurity that inhibits crystallization.

14. A method of purifying a pesticide comprising:
a) melting a pesticide having a melting point not more than about 90° C., wherein the pesticide comprises at least one active ingredient and at least one impurity capable of inhibiting crystallization;
b) coating the melted pesticide on a substrate to form a pesticide particle;
c) substantially reducing the amount of crystallization inhibiting impurity by an azeotropic method; and
d) crystallizing the pesticide.

15. The method of claim 14, wherein the active ingredient is methyl N-(2-{[1-(4-chlorophenyl)-1H-pyrazol-3-yl]oxymethyl}phenyl)N-methoxy carbamate.

16. The method of claim 14, wherein the method further comprises mixing the pesticide with a solvent before coating the pesticide on the substrate.

17. The method of claim 14, wherein the active ingredient chemically decomposes at temperatures within 50° C. of the normal boiling point of the impurity.

18. The method of claim 14, wherein the azeotropic method is accomplished by vacuum distillation, heat, or low pressure evaporation.

19. The method of claim 14, wherein the crystallized pesticide has a particle size of not more than 10 μm.

20. The method of claim 14, wherein the crystallized pesticide comprises less than 0.1 wt. % of an impurity that inhibits crystallization.

* * * * *

UNITED STATES PATENT AND TRADEMARK OFFICE
CERTIFICATE OF CORRECTION

PATENT NO. : 7,247,175 B2  
APPLICATION NO. : 10/397765  
DATED : July 24, 2007  
INVENTOR(S) : Finch et al.

Page 1 of 1

It is certified that error appears in the above-identified patent and that said Letters Patent is hereby corrected as shown below:

In claim 4, column 10, indicated line 66:
"4chlorophenyl" should read --4-chlorophenyl--

In claim 9, column 11, indicated line 14:
"diato mite" should read --diatomite--

Signed and Sealed this

First Day of April, 2008

JON W. DUDAS
*Director of the United States Patent and Trademark Office*